United States Patent [19]

Kondo et al.

[11] 3,970,671

[45] July 20, 1976

[54] CHROMOGENIC COMPOUNDS AND METHOD FOR PREPARATION THEREOF

[75] Inventors: Mitsuru Kondo, Kawanishi; Makoto Miyake, Nishinomiya; Hiroshi Iwasaki, Takatsuki, all of Japan

[73] Assignee: Kanzaki Paper Manufacturing Co., Ltd., Tokyo, Japan

[22] Filed: July 23, 1974

[21] Appl. No.: 491,133

Related U.S. Application Data

[63] Continuation-in-part of Ser. No. 282,055, Aug. 21, 1972, abandoned.

[30] Foreign Application Priority Data

Aug. 21, 1971  Japan............................... 46-63830
Nov. 16, 1971  Japan............................... 46-92047

[52] U.S. Cl................................ 260/335; 282/27.5; 428/488
[51] Int. Cl.$^2$...................................... C07D 493/10
[58] Field of Search...................... 282/55; 260/335

[56] References Cited
UNITED STATES PATENTS

| | | | |
|---|---|---|---|
| 3,244,549 | 4/1966 | Farnham et al. | 117/36.2 |
| 3,627,787 | 12/1971 | Lin | 260/335 |
| 3,654,314 | 4/1972 | Farber et al. | 260/335 |
| 3,691,203 | 9/1972 | Koga et al. | 260/335 |
| 3,694,461 | 9/1972 | Farber et al. | 260/335 |
| 3,787,325 | 1/1974 | Hoover | 260/335 |
| 3,839,361 | 10/1974 | Terayama et al. | 260/335 |

FOREIGN PATENTS OR APPLICATIONS 2,001,864  7/1970  Germany

Primary Examiner—Norma S. Milestone
Attorney, Agent, or Firm—Cushman, Darby & Cushman

[57] ABSTRACT

Chromogenic compounds for use in pressure sensitive recording sheets represented by the formula:

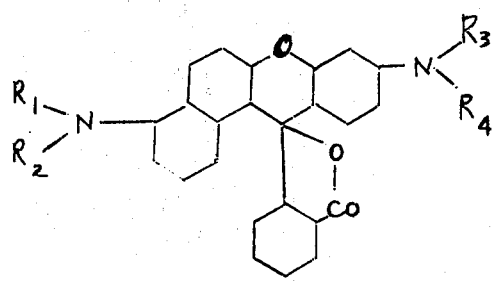

are disclosed, wherein $R_1$ and $R_2$ are independently, hydrogen substituted or unsubstituted lower alkyl, aliphatic acyl, phenyl substituted aliphatic acyl, benzoyl, aralky, phenyl (the benzene nuclei of those substituents may be further substituted by chlorine, bromine, lower alkyl, lower alkoxy or nitro), allyl, allyl substituted by lower alkyl or phenyl, propargyl, or propargyl substituted by lower alkyl or a phenyl; $R_3$ and $R_4$ are independently lower alkyl, benzyl and phenyl (the benzene nuclei or those substiutents may be further substituted by chlorine, bromine, lower alkyl or lower alkoxy), either $R_1$ or $R_2$ being other than hydrogen when $R_3$ and $R_4$ are both ethyl groups.

2 Claims, No Drawings

CHROMOGENIC COMPOUNDS AND METHOD FOR PREPARATION THEREOF

CROSS REFERENCE TO RELATED APPLICATION

This application is a continuation-in-part of our earler co-pending application Ser. No. 282,055 filed 21st Aug. 1972 and now abandoned.

BACKGROUND OF THE INVENTION

This invention relates to novel chromogenic compounds for use in recording sheet which develops color images by an electron donor-acceptor color-forming reaction between chromogenic compounds and acidic materials which react upon contact to produce a color.

More particularly, this invention relates to chromogenic compounds which can be classified as benz [a] fluorans, methods for the preparation thereof and the recording sheets containing the same as chromogenic materials.

Heretofore oil carbon papers have been widely used for duplicating documents and slips as office work materials. The carbon paper duplicating system is advantageous in that it is liable to stain clothes and hands and in that it is troublesome to insert the oil carbon paper between documents and slips.

In order to eliminate the inefficiencies and defects of the oil carbon paper, pressure-sensitive copying paper or noncarbon paper, which is economic and handy, has recently made its debut in place of the oil carbon paper complying with demand for speed-up of office works.

In the pressure-sensitive recording sheet utilized is an electron donor-acceptor color-forming reaction between colorless chromogenic materials such as crystal violet lactone and acidic electron acceptor such as acid clay, attapalgite, zeolite, kaolin, organic acid (e.g. salicylic acid), bisphenol-A, phenol-formalin resin, hydrolized maleic anhydride-styrene copolymer. Triphenylmethane compounds such as crystal violet lactone are usually used as chromogenic compounds for such purpose. Crystal violet lacone changes in color from colorless to vivid bluish violet when it is brought to contact with the electron-acceptor.

The triphenylmethane compounds used in the above mentioned pressure sensitive recording sheet have an inherent disadvantage that they are so unstable against sunlight that the colored images formed in contact with an electron-acceptor tend to disappear by the effect of sunlight or ultraviolet light in a short period of time. Further, triphenyl methane lactones are liable to be affected by water or moisture, that is, the droplets of water prevent the lactone ring from cleavage, so that the color images obtained by the opening of lactone ring tend to disappear by the effect of water or moisture.

Recently, attempts have been made to obtain improved pressure-sensitive copy sheets which provide black color images. For this purpose, several chromogenic compounds which produce various colors, for example, red, blue, yellow and etc. on contact with an electron-acceptor are mixed to use.

But this method is disadvantageous in that the process for making a coating color is so complicated and in that those various chromogenic compounds have different color deepness its color shade and different color developing speed, due to their different basic structures, therefore, the produced color images tend to change in shade, e.g., from black to reddish black, as time passes.

The primary object of the invention is to provide novel chromogenic compounds in which the above mentioned disadvantages can be avoided.

Another object of the invention is to provide useful methods for preparing such novel compounds.

A further object of the invention is to provide new and improved markforming record sheet utilizing chromogenic compounds which react with acidic materials upon contact to produce colors.

Other objects of the invention will be partly obvious and will partly become apparent from the following descriptions.

SUMMARY OF THE INVENTION

The compounds of the present invention, which can be classified as benz [a] fluorans, are represented by the following general formula:

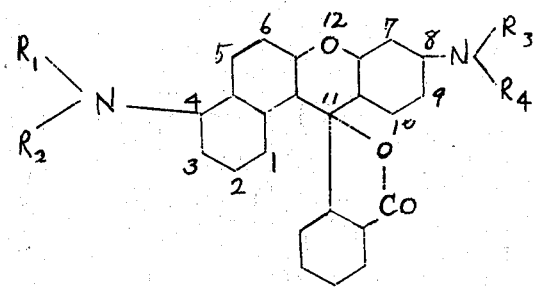

wherein $R_1$ and $R_2$ are independently, hydrogen, substituted or unsubstituted lower alkyl, lower aliphatic acyl, phenyl substituted aliphatic acyl, benzoyl, aralkyl, phenyl (the benzen nuclei of said substituents may be further substituted by chlorine, bromine, lower alkyl, lower alkoxy or nitro), allyl, allyl substituted by lower alkyl or phenyl, propargyl or propargyl substituted by lower alkyl or phenyl; and $R_3$ and $R_4$ are independently lower alkyl, benzyl, phenyl, the benzen nuclei of each of which may be substituted by chlorine, bromine, lower alkyl or lower alkoxy, provided that either $R_1$ or $R_2$ is other than hydrogen when both $R_3$ and $R_4$ are ethyl.

Preferred examples of the compounds represented by the above formulae will be given in the Detailed Description of the Invention and in the Detailed Description of the Preferred Embodiments hereinafter.

The compounds of the invention can be conveniently prepared by reacting an amino-2-naphthol represented by the formula,

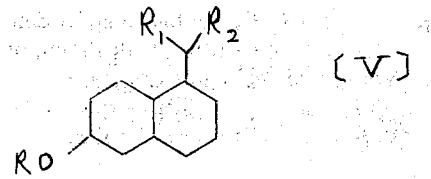

[V]

wherein R is hydrogen or lower alkyl, with 2-(2-hydroxy-4-aminobenzoyl)benzoic acid represented by the formula,

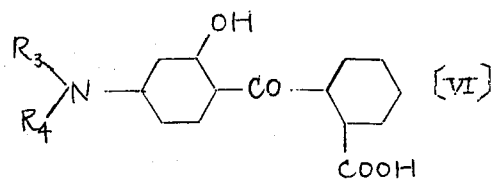

In the formulae [V] and [VI], $R_1$, $R_2$, $R_3$ and $R_4$ are the same as defined in the above general formula.

Alternatively, the compounds of the invention may be conveniently prepared by reacting a compound represented by the formula,

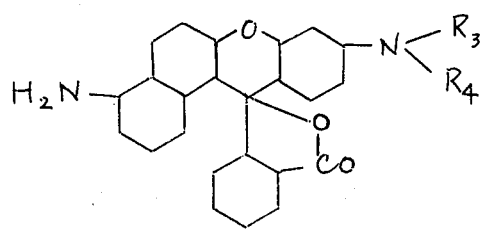

or

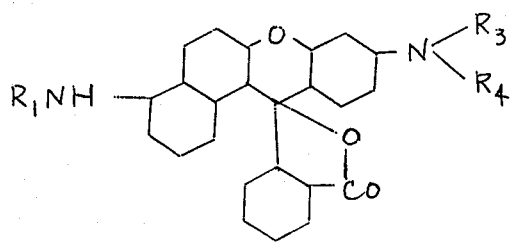

wherein $R_1$, $R_3$ and $R_4$ are the same as defined in the above general formula with an alkylating or acylating agent represented by the formula, $$R_2X \quad\quad [IX]$$

wherein $R_2$ is the same as defined in the general formula and X is a residue of alkylating or acylating agent.

The mark-forming record sheet according to the invention contains as a chromogenic component at least one compound represented by the above mentioned formula [I]. Preferably, the record sheet is a pressure-sensitive record sheet comprising color-forming components (i.e. chromogenic compound and acidic material) on and/or within one or more sheet supports, the color-forming components being isolated from one another by a pressure-rupturable barrier. The record sheet may be a pressure-sensitive record sheet comprising color-forming components on and/or within one or more sheet supports, both of chromogenic material and acidic material being isolated from liquid solvent by a pressure-rupturable barrier. In another embodiment of the invention the record sheet is a thermo-responsive record sheet comprising a supporting sheet having chromogenic material and a phenolic material solid at room temperature but capable of liquefying and/or vaporizing at normal thermographic temperature. The sheet material may be coated thereon and/or impregnated therein with coating composition containing at least one fluoran compound represented by the formula [I].

DETAILED DESCRIPTION OF THE INVENTION

The compounds of the invention have technical advances over prior arts in the following points.

a. The fluoran compounds of the invention are colorless and very soluble in a non-polar, non-volatile solvent used for preparing a recording sheet as a carrier material. Among those solvents there may be included olive oil, castor oil, paraffin oil, alkylated diphenyl, alkylated diphenylmethane, alkylated naphthalene, chlorinated paraffin, tricresyl phosphate and the like. Such good solubility in these solvents is probably caused by the naphthalene ring in the benz[a]flouran represented by the general formula [I]. Good solubility particularly in the aromatic solvents makes it easy to control the concentration of chromogenic compounds.

b. The present fluoran compounds produce a dark and deep color, which makes it easy to obtain a deep vivid color image with use of a small amount of them. These fluoran compounds show various sorts of dark color, for example, dark red, deep reddish violet, deep bluish violet, dark blue-black or dark blue according to the number, kind and position of the substituents. The present fluoran compounds have almost the same color developing speed, so that the pressure-sensitive recording sheet obtained by mixing the present fluoran compounds produces a black color and shows no lag of the color developing time and no changes of the color images.

c. The present fluoran compounds have high color-developing speed. Color formation occurs immediately when the fluoran compounds in the form of a solution in the above-mentioned solvents are brought into contact with acidic electron-acceptor such as acid clay, silica gel, activated clay, salicylic acid, bis phenyl-A, phenolic resin and the like. Thus obtained colored images endure storage for a long period of time without disappearance or change in color due to moisture or droplets of water. It is considered that such high color-developing speed and high water resistance are probably caused by the naphthalene ring in the fluoran nucleus.

perferably be used. If necessary, carbon disulfide, chlorinated benzen or nitrobenzen may be used as a solvent for the reaction system.

In order to convert the resulting xanthohydrol [X] to the fluoran compound [I] by closing the ring, the xanthohydrol may be dissolved and heated in a solvent at a temperature of 50°C to 150°C, and then the mixture may be cooled to obtain the fluoran compounds as white crystal.

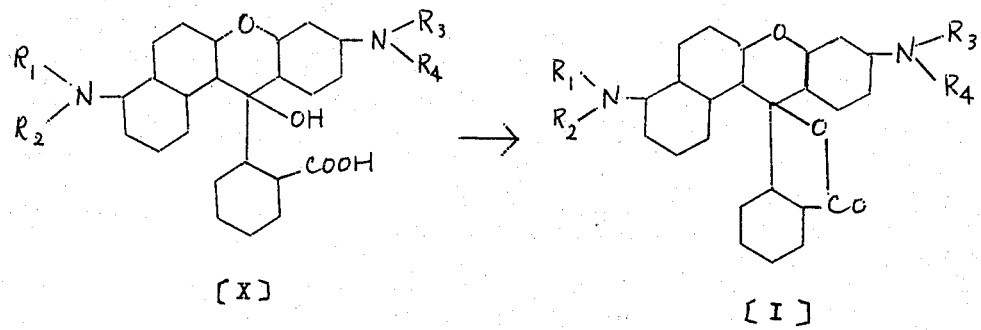

d. The pressure-sensitive recording sheet prepared with use of these fluoran compounds gives deep colors, for example, dark red, dark reddish violet, bluish violet or dark blue, on the surface of the sheet at the moment when the present fluoran compounds are brought into contact with acidic electron-acceptor by application of pressure onto the sheet by means of a pencil or a typewriter. The obtained color images on the sheet have so high water resistance and also high light resistance so that they do not disappear or change in color due to moisture or droplets of water, or by exposure to sunlight for a prolonged period of time.

The present benz [a] fluoran compounds represented by the general formula [I] may be prepared according to any of the following two different synthetic routes.

According to the first synthetic route, amino-2-naphthol represented by the formula [V] is made to react with 2-(4-amino-2-hydroxybenzoyl)benzoic acid represented by the formula [VI] at a temperature within the range of 20° to 180°C for several hours. The resultant is poured into ice water, and if necessary, the solvent is removed, and the colored solid material is obtained by filtration after neutralization with sodium hydroxide or potassium hydroxide. The obtained compound is 11-(2'-carboxyphenyl)diaminobenzo [a]xanthohydrol represented by the formula [X].

Among the useful solvents for the ring-closure reaction system, there may be included aromatic hydrocarbons such as benzene and xylene, halogenated aromatic hydrocarbons such as chlorobenzene, bromobenzene, dichlorobenzene and trichlorobenzene, alcohols such as methanol and ethanol, amides such as dimethylformamide and diethylformamide, sulfoxides such as dimethylsulfoxide and diethylsulfoxide, aliphatic hydrocarbons such as n-hexane and cyclohexane, halogenated aliphatic hydrocarbons such as chloroform, bromoform and methylchloroform, ethers such as dimethyl ether and diethyl ether.

The cyclization may often be facilitated by the addition of aliphatic amines such as dimethylamine, trimethylamine, diethylamine, triethylamine, aliphatic aminoalcohols such as ethanolamine, propanol-amine, or, hetrocyclic basic substances such as pyridine, picoline.

White crystals, which are separated on heating and cooling in anyone of these cyclization solvents or a mixture thereof, refiltered and washed with a non-polar solvent such as cyclohexane, n-hexane or diethyl ether to obtain a colorless compound represented by the formula [I]. In case of compounds having a stable lactone ring, white crystals may often be obtained merely

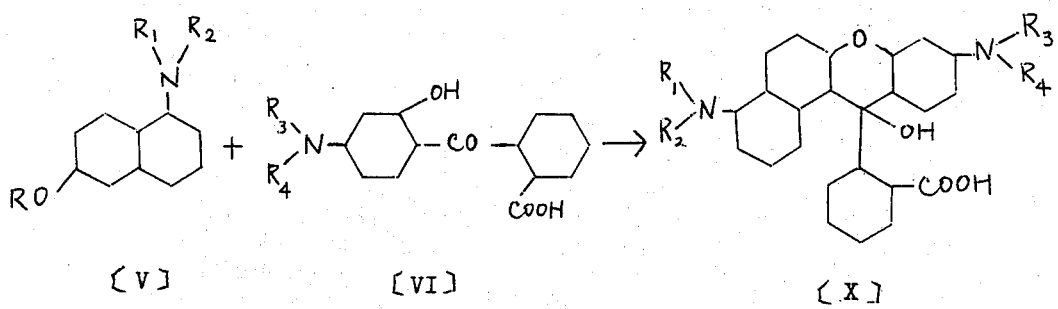

As dehydrating-condensing-agents, sulfuric acid, phosphrous pentoxide, phosphoric acid, polyphosphoric acid, anhydrous metal chlorides such as anhydrous tin chloride, anhydrous zinc chloride, anhydrous alminum chloride or anhydrous ferric chloride, phosphoric trichloride or phosphoric pentachloride may by neutralizing a hydrochloric acid or sulfuric acid solution dissolving those compounds therein with caustic soda, potassium hydroxide, etc.

The alternative synthetic route utilizes the fluoran compounds represented by any of the following formulae:

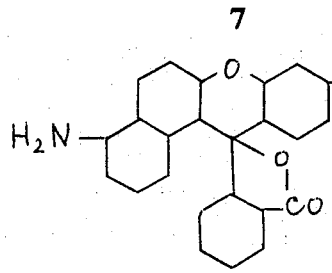
[X']
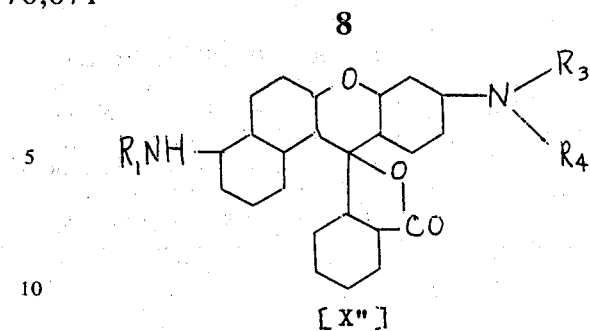
[X'']
The benz [a] fluoran represented by the above formula [X'] or [X''] may be prepared according to the before mentioned first synthesis route for obtaining the compound represented by [X]. That is to say:
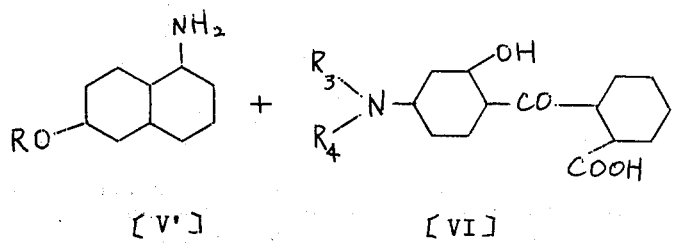
[V']  [VI]
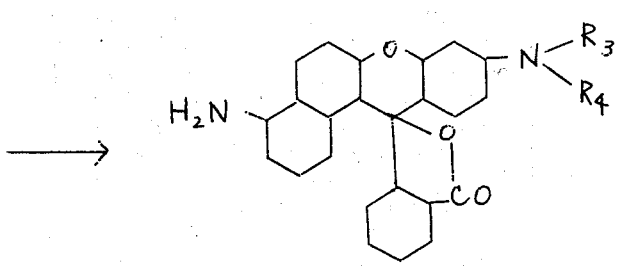
[X']
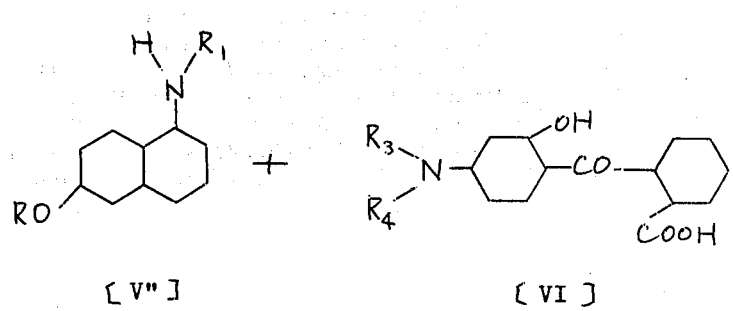
[V'']  [VI]
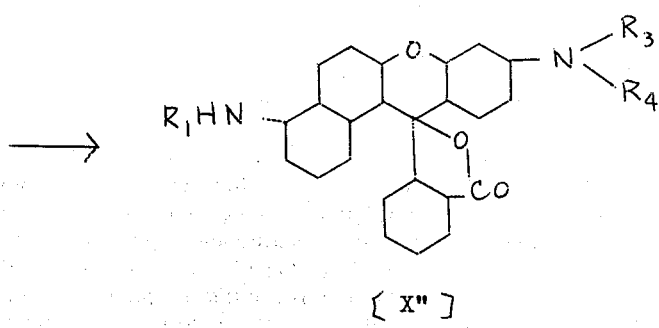
[X'']

In the above it will be appreciated that the compounds represented by the formula [V'] and [V"] are the examples of the compounds represented by the formula [V], for the cases where each of $R_1$ and $R_2$ is hydrogen, and $R_2$ is hydrogen, respectively. The benz [a] fluoran represented by the formula [X'] or [X] is then treated with an alkylating agent or acylating agent represented by the formula $R_2X$ to obtain the fluoran compound represented by the formula [I]. The reaction is as follows:

Among the preferred acylating agents which may be used in the above-mentioned reaction the following compounds may be included:
Acetic anhydride,
Propionic anhydride,
Butyric anhydride,
Acrylic anhydride,
Propiolic anhydride,
Crotonic anhydride,
Cinnamic anhydride,
Benzoic anhydride,

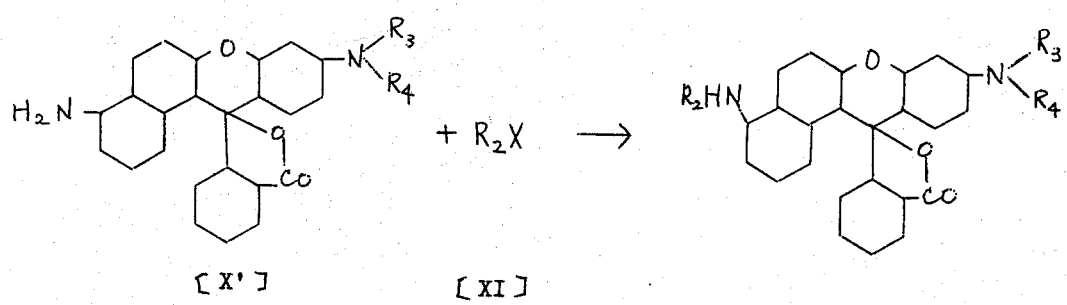

or

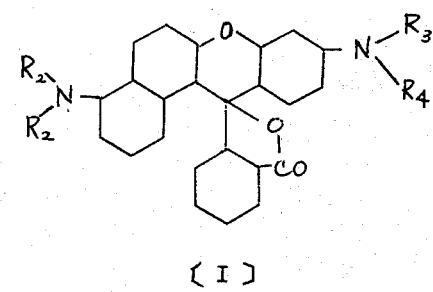

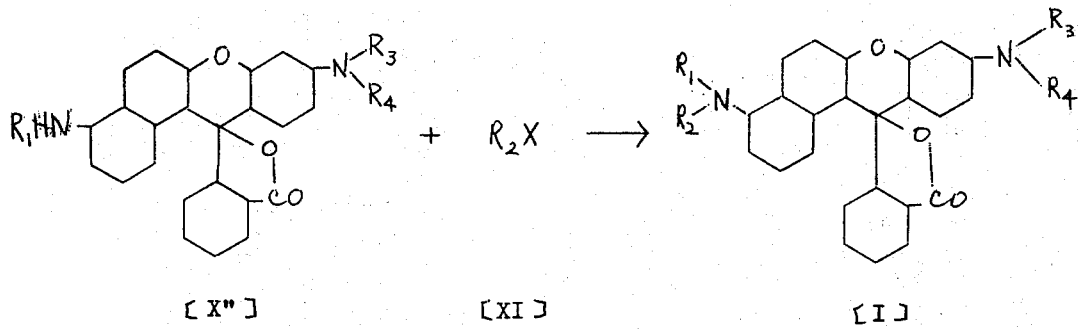

In the formula for the alkylating agent or acylating agent, $R_2$ is the same as defined hereinbefore and X is halogen, hydroxy, $SO_4^{--}$, $PO_3^{---}$, sulfonyloxy, acyloxy, benzoyloxy or active double bond group. The above reactions may preferably carried out at a temperature of 30°–150°C for several hours, if desired, in the presence of a solvent and a dehydrohalogenating agent. The purification process after the reaction is the same as that in the before mentioned first route.

p-Chlorobenzoic anhydride,
m-Chlorobenzoic anhydride,
o-Chlorobenzoic anhydride,
p-Nitrobenzoic anhydride,
m-Nitrobenzoic anhydride,
o-Nitrobenzoic anhydride,
p-Bromobenzoic anhydride,
m-Bromobenzoic anhydride,
o-Bromobenzoic anhydride, p-Methylbenzoic anhydride,
m-Methylbenzoic anhydride,
o-Methylbenzoic anhydride
p-Methoxybenzoic anhydride,
m-Methoxybenzoic anhydride,
o-Methoxybenzoic anhydride
Acetyl chloride,
Propionyl chloride,
Butyryl chloride,
Acryloyl chloride,
Propiolyl chloride,
Methacryloyl chloride,
Crotonoyl chloride,
Cinnamoyl chloride,
Acetyl bromide,
Butyryl bromide,
Propiolyl bromide,
Crotonyl bromide,
Acryloyl bromide,
Methacryloyl bromide,
Cinnamoyl bromide,
Benzoyl chloride
p-Chlorobenzoyl chloride,
m-Chlorobenzoyl chloride,
o-Chlorobenzoyl chloride,
p-Nitrobenzoyl chloride,
m-Nitrobenzoyl chloride,
o-Nitrobenzoyl chloride,
p-Bromobenzoyl chloride,
m-Bromobenzoyl chloride,
o-Bromobenzoyl chloride,
p-Methylbenzoyl chloride,
m-Methylbenzoyl chloride,
o-Methylbenzoyl chloride,
p-Methoxybenzoyl chloride,
m-Methoxybenzoyl chloride,
o-Methoxybenzoyl chloride,
Benzoyl bromide,
p-Chlorobenzoyl bromide,
m-Chlorobenzoyl bromide,
o-Chlorobenzoyl bromide,
p-Nitrobenzoyl bromide,
m-Nitrobenzoyl bromide,
o-Nitrobenzoyl bromide,
p-Bromobenzoyl bromide,
m-Bromobenzoyl bromide,
o-Bromobenzoyl bromide,
p-Methylbenzoyl bromide,
m-Methylbenzoyl bromide,
o-Methylbenzoyl bromide,
p-Methoxybenzoyl bromide,
m-Methoxybenzoyl bromide and
o-Methoxybenzoyl bromide As the alkylating agent, the following compounds are preferably used:
Esters such as
Dimethyl sulfate,
Diethyl sulfate,
Dipropyl sulfate,
Dibutyl sulfate,
Trimethyl phosphate,
Triethyl phosphate,
Tripropyl phosphate,
Methyl benzenesulfonate,
Ethyl benzenesulfonate,
Propyl benzene sulfonate,
Methyl p-toluenesulfonate,
Ethyl p-toluenesulfonate,
Propyl p-toluenesulfonate,
Methoxyethyl p-toluenesulfonate,
Ethoxyethyl p-toluenesulfonate,
Methyl methanesulfonate and
Propyl methanesulfonate,
Lower alkyl halides such as
Methyl chloride,
Methyl bromide,
Ethyl chloride,
Ethyl bromide,
Propyl chloride,
Propyl bromide,
Butyl chloride and
Butyl bromide
Benzyl halides such as
Benzyl chloride,
p-Nitrobenzyl chloride,
m-Nitrobenzyl chloride,
o-Nitrobenzyl chloride,
p-Chlorobenzyl chloride,
m-Chlorobenzyl chloride,
o-Chlorobenzyl chloride,
p-Bromobenzyl chloride,
m-Bromobenzyl chloride,
o-Bromobenzyl chloride,
p-Methylbenzyl chloride,
m-Methylbenzyl chloride,
o-Methylbenzyl chloride,
p-Methoxybenzyl chloride,
m-Methoxybenzyl chloride,
o-Methoxybenzyl chloride,
Benzyl bromide,
p-Nitrobenzyl bromide,
m-Nitrobenzyl bromide,
o-Nitrobenzyl bromide,
p-Chlorobenzyl bromide,
m-Chlorobenzyl bromide,
o-Chlorobenzyl bromide,
p-Bromobenzyl bromide,
m-Bromobenzyl bromide,
o-Bromobenzyl bromide,
p-Methylbenzyl bromide,
m-Methylbenzyl bromide,
o-Methylbenzyl bromide,
p-Methoxybenzyl bromide,
m-Methoxybenzyl bromide and
o-Methoxybenzyl bromide,
Allyl halides such as
Allyl chloride,
Allyl bromide,
2-Methylallyl chloride,
2-Methylallyl bromide,
2-Ethylallyl chloride,
2-Ethylallyl bromide,
2-Butenyl chloride,
2-Butenyl bromide,
Cinnamyl chloride and
Cinnamyl bromide,
Propargyl halide derivatives such as
Propargyl chloride,
Propargyl bromide,
2-Butynyl chloride,
2-Butynyl bromide,
2-Pentynyl chloride,
2-Pentynyl bromide,
3-Phenyl-2-propynyl chloride and
3-Phenyl-2-propynyl bromide,
Acrylonitrile, and Acrylamide.

As the dehydrohalogenating agent,
Sodium hydrogen carbonate
Potassium hydrogen carbonate
Sodium carbonate
Potassium carbonate
Sodium acetate
Potassium acetate
and
Caustic soda
may be used. Also, if circumstances permit the basic substance used in the ring-closing step or the fluoran compound represented by the formula [X'] may be used in an access amount.

Among the compounds used as the solvent in the second route, there may be included aromatic hydrocarbon solvents such as benzene, xylene, etc.; halogenated aliphatic hydrocarbon solvents such as chloroform, bromoform, methylchloroform, etc.; halogenated aromatic hydrocarbon solvents such as chlorobenzene, bromobenzene, dichlorobenzenes, etc.; alcohol solvents such as methanol, ethanol, propanol, etc.; ether solvents such as diethyl ether, dimethylene glycol, dimethyl ether, diethylene glycol, etc.; sulfoxide solvents such as dimethyl sulfoxide, diethyl sulfoxide, etc.; and amide solvents such as N,N'-dimethylformamide, dimethylacetamide, N-methylpyrrolidone.

Specific examples of the compounds produced by the above-mentioned methods according to the present invention are given with the respective shades on silica gel after development as follows:

| Compound | Shade after development |
| --- | --- |
| 4-amino-8-dimethylaminobenz[a]fluoran | bluish violet |
| 4-amino-8-dipropylaminobenz[a]fluoran | " |
| 4-methylamino-8-dimethylaminobenz[a]fluoran | blue |
| 4-ethylamino-8-dimethylaminobenz[a]fluoran | " |
| 4-propylamino-8-diethylaminobenz[a]fluoran | " |
| 4-dimethylamino-8-dimethylaminobenz[a]fluoran | reddish violet |
| 4-diethylamino-8-dimethylaminobenz[a]fluoran | " |
| 4-dimethylamino-8-diethylaminobenz[a]fluoran | " |
| 4-dipropylamino-8-dimethylaminobenz[a]fluoran | " |
| 4-benzylamino-8-dimethylaminobenz[a]fluoran | blue |
| 4-(4-nitrobenzyl)amino-8-diethylaminobenz[a]fluoran | " |
| 4-dibenzylamino-8-dimethylaminobenz[a]fluoran | reddish violet |
| 4-dibenzylamino-8-diethylaminobenz[a]fluoran | " |
| 4-(4-methylabenzyl)amino-8-dimethylaminobenz[a]fluoran | blue |
| 4-diallylamino-8-dimethylaminobenz[a]fluoran | reddish violet |
| 4-diallylamino-8-diethylaminobenz[a]fluoran | " |
| 4-dipropargylamino-8-dimethylaminobenz[a]fluoran | " |
| 4-dipropargylamino-8-diethylaminobenz[a]fluoran | " |
| 4-cinnamylamino-8-diethylaminobenz[a]fluoran | blue |
| 4-dicinnamylamino-8-dimethylaminobenz[a]fluoran | reddish violet |
| 4-dimethacryloylamino-8-diethylaminobenz[a]fluoran | " |
| 4-dicrotylamino-8-diethylaminobenz[a]fluoran | " |
| 4-dicrotylamino-8-dimethylaminobenz[a]fluoran | " |
| 4-acetylamino-8-dimethylaminobenz[a]fluoran | dark red |
| 4-(N-acetyl-N-methyl)amino-8-diethylaminobenz[a]fluoran | " |
| 4-(N-acetyl-N-methyl)amino-8-diethylaminobenzbenz[a]fluoran | " |
| 4-(N-acetyl-N-allyl)amino-8-diethylaminobenz[a]fluoran | " |
| 4-N-benzoylamino-8-dimethylaminobenz[a]fluoran | " |
| 4-N-(4-chlorobenzoyl)amino-8-dipropylaminobenz[a]fluoran | " |
| 4-N-cinnamoylamino-8-dipropylaminobenz[a]fluoran | " |
| 4-(N-buthyryl-N-propyl)amino-8-diethylaminobenz[a]fluoran | " |
| 4-(N-acryloyl-N-ethyl)amino-8-dimethylaminobenz[a]fluoran | dark red |
| 4-(N-propionyl-N-benzyl)amino-8-dimethylaminobenz[a]fluoran | " |
| 4-(N-acetyl-N-cinnamyl)amino-8-dimethylaminobenz[a]fluoran | " |
| 4-amino-8-(N-methyl-N-phenyl)aminobenz[a]fluoran | bluish violet |
| 4-amino-8-(N-ethyl-N-phenyl)aminobenz[a]fluoran | " |
| 4-amino-8-(N-propyl-N-phenyl)aminobenz[a]fluoran | " |
| 4-amino-8- N-methyl-N-(p-methylphenyl) aminobenz[a]fluoran | " |
| 4-amino-8-{N-ethyl-N-(p-methylphenyl)}aminobenz[a]fluoran | " |
| 4-amino-8-{N-propyl-N-(p-methylphenyl)}aminobenz[a]fluoran | " |
| 4-amino-8{N-methyl-N-(p-ethylphenyl)}aminobenz[a]fluoran | " |
| 4-amino-8-{N-ethyl-N-(p-ethylphenyl)}aminobenz[a]fluoran | bluish violet |
| 4-amino-8-{N-propyl-N-(p-ethylphenyl)}aminobenz[a]fluoran | " |
| 4-amino-8-{N-methyl-N-(2',4'-dimethylphenyl)}-aminobenz[a]fluoran | " |
| 4-amino-8-{N-propyl-N-(2,4-dimethylphenyl)}-aminobenz[a]fluoran | bluish violet |
| 4-amino-8-{N-ethyl-N-(p-chlorophenyl)}amino- | |

| Compound | -continued<br>Shade after development |
|---|---|
| benz[a]fluoran | |
| 4-amino-8-{N-methyl-N-(p-chlorophenyl)}amino-benz[a]fluoran | " |
| 4-amino-8-{N-propyl-N-(p-chlorophenyl)}amino-benz[a]fluoran | " |
| 4-methylamino-8-(N-methyl-N-phenyl)aminobenz-[a]fluoran | " |
| 4-methylamino-8-(N-ethyl-N-phenyl)aminobenz-[a]fluoran | blue black |
| 4-methylamino-8-(N-propyl-N-phenyl)aminobenz-[a]fluoran | " |
| 4-ethylamino-8-{N-methyl-N-(p-methylphenyl)}-aminobenz[a]fluoran | " |
| 4-ethylamino-8-{N-ethyl-N-(p-methylphenyl)}-aminobenz[a]fluoran | " |
| 4-methylamino-8-{N-methyl-N-(2,4-dimethylphenyl)}-aminobenz[a]fluoran | " |
| 4-methylamino-8-{N-ethyl-N-(2,4-dimethylphenyl)}-aminobenz[a]fluoran | " |
| 4-ethylamino-8-{N-methyl-N-(2,4-dimethyl}-phenyl) aminobenz[a]fluoran | " |
| 4-ethylamino-8-{N-ethyl-N-(2,4-dimethyl}-phenyl) aminobenz[a]fluoran | " |
| 4-dimethylamino-8-(N-methyl-N-phenyl)amino-benz[a]fluoran | " |
| 4-dimethylamino-8-(N-ethyl-N-phenyl)amino-benz[a]fluoran | reddish violet |
| 4-diethylamino-8-{N-methyl-N-(p-methylphenyl)}-aminobenz[a]fluoran | " |
| 4-diethylamino-8-{N-ethyl-N-(p-methylphenyl)}-aminobenz[a]fluoran | " |
| 4-propylamino-8-(N-methyl-N-phenyl)aminobenz-[a]fluoran | blue black |
| 4-propylamino-8-(N-ethyl-N-phenyl)aminobenz-[a]fluoran | " |
| 4-propylamino-8-{N-methyl-N-(p-methylphenyl)}-aminobenz[a]fluoran | " |
| 4-propylamino-8-{N-ethyl-N-(p-methylphenyl)}-aminobenz[a]fluoran | " |
| 4-dipropylamino-8-{N-methyl-N-(p-methylphenyl)}-aminobenz[a]fluoran | reddish violet |
| 4-dipropylamino-8-{N-ethyl-N-(p-methylphenyl)}-aminobenz[a]fluoran | " |
| 4-benzylamino-8-{N-methyl-N-(p-methylphenyl)}-aminobenz[a]fluoran | blue black |
| 4-benzylamino-8-{N-ethyl-N-(p-methylphenyl)}-aminobenz[a]fluoran | " |
| 4-dibenzylamino-8-{N-methyl-N-(p-methylphenyl)}-aminobenz[a]fluoran | reddish violet |
| 4-dibenzylamino-8-{N-ethyl-N-(p-methylphenyl)}-aminobenz[a]fluoran | " |
| 4-phenylamino-8-{N-methyl-N-(p-methylphenyl)}-aminobenz[a]fluoran | blue black |
| 4-phenylamino-8-{N-ethyl-N-(p-methylphenyl)}-aminobenz[a]fluoran | " |
| 4-(N-methyl-N-phenyl)amino-8-{N-methyl-N-(p-methylphenyl)}aminobenz a fluoran | reddish violet |
| 4-(N-methyl-N-phenyl)amino-8-{N-ethyl-N-(p-methylphenyl)}aminobenz a fluoran | " |
| 4-(N-ethyl-N-phenyl)amino-8-{N-methyl-N-(p-methylphenyl)}aminobenz a fluoran | " |
| 4-(N-ethyl-N-phenyl)amino-8-{N-ethyl-N-(p-methylphenyl)}aminobenz a fluoran | " |
| 4-(p-methylphenyl) amino-8-{N-methyl-N-(p-methylphenyl)}aminobenz a fluoran | blue black |
| 4-(p-methylphenyl)amino-8-{N-ethyl-N-(p-methylphenyl)}aminobenz a fluoran | " |
| 4-{N-methyl-N-(p-methylphenyl)}amino-8-{N-methyl-N-(p-methylphenyl)}aminobenz a fluoran | reddish violet |
| 4-{N-methyl-N-(p-methylphenyl)}amino-8-{N-ethyl-N-(p-methylphenyl)}aminobenz a fluoran | " |
| 4-{N-ethyl-N-(p-methylphenyl)}amino-8-{N-ethyl-N-(p-methylphenyl)}aminobenz a fluoran | " |
| 4-diallylamino-8-{N-ethyl-N-(p-methylphenyl)}-aminobenz a fluoran | " |
| 4-dipropargylamino-8-{N-ethyl-N-(p-methyl-phenyl)}aminobenz a fluoran | " |
| 4-dicinnamylamino-8-{N-ethyl-N-(p-methylphenyl)}-aminobenz a fluoran | " |
| 4-dimethacrylamino-8-{N-ethyl-N-(p-methylphenyl)}aminobenz a fluoran | " |
| 4-dicrotylamino-8-{N-ethyl-N-(p-methylphenyl)}-aminobenz a fluoran | " |
| 4-acetylamino-8-{N-ethyl-N-(p-methylphenyl)}-aminobenz[a]fluoran | dark red |
| 4-(N-acetyl-N-methylamino)-8-{N-ethyl-N-(p-methylphenyl)}aminobenz[a]fluoran | " |
| 4-acetylamino-8-{N-methyl-N-2',4'-dimethyl-phenyl)}aminobenz[a]fluoran | " |
| 4-benzoylamino-8-{N-methyl-N-(2',4'-dimethyl-phenyl)}aminobenz[a]fluoran | dark red |
| 4-(N-benzoyl-N-methyl)amino-8-{N-methyl-N- | |

| Compound | -continued<br>Shade after development |
|---|---|
| (2',4'-dimethylphenyl)}aminobenz[a]fluoran | " |
| 4-cinnamoylamino-8-{N-methyl-N-(p-chlorophenyl)}<br>aminobenz[a]fluoran | " |
| 4-butyrylamino-8-{N-methyl-N-(p-chlorophenyl)}-<br>aminobenz[a]fluoran | " |
| 4-acryloylamino-8-{N-methyl-N-(p-chlorophenyl)}-<br>aminobenz[a]fluoran | " |
| 4-propionylamino-8-{N-methyl-N-(p-chlorophenyl)}-<br>aminobenz[a]fluoran | " |
| 4-(2',4',6'-trimethylphenyl)amino-8-{N-methyl-<br>N-(o-methoxyphenyl)}aminobenz[a]fluoran | blue black |
| 4-(2',4',6'-trimethylphenyl)amino-8-{N-ethyl-<br>N-(o-methoxyphenyl)}aminobenz[a]fluoran | " |

There are several types of recording systems already known utilizing an electron donor-acceptor color-forming reaction between chromogenic material and acidic material. The pressure-sensitive recording systems generally comprise color-forming components on and/or within one or more sheet supports, the color-forming components being isolated from one another by a pressure-rupturable barrier. Where the color-forming components are disposed on separate sheets as disclosed in U.S. Pat. No. 2,712,507, the record material referred to as a "transfer" or "couplet" system. In such system, a solution of a chromogenic material is held in rupturable microscopic capsules coated onto one surface of a transfer sheet, while an adjacent receiving sheet is sensitized with an acidic material, i.e. an electron-acceptor. Most common acidic materials are activated acid clay and acid clays, such as attapulgite, zeolite, bentonite, kaolin and silica. Recently, monomeric phenols or acid reactant polymeric materials, such as phenolic polymers, phenol acetylene polymers, maleic acid-rosin resins, have been suggested either alone or in combination with acid clays.

In the manufacturing method of such record material, for instance, a non-volatile oil containing a chromogenic material dissolved therein is protected by encapsulation with coacervate film of a water-soluble polymer. The resulting coating composition containing dispersed capsules are coated on one side of a sheet, and coating composition of said electron-acceptors is coated on the other side of the sheet. When several sheets are laid one over another and impressed with a pencil or the like, capsules are collapsed to release the oil containing chromogenic material which produces a duplicated image on contact with the electron-acceptor. In another system as disclosed in U.S. Pat. No. 2,730,457, a coating liquid containing both of the capsules chromogenic material and acidic material is applied on one side of a sheet or alternatively, a coating containing capsule is first applied on one side of a sheet and the second coating containing the electron-acceptor is applied thereon. Thus, all the components are disposed on a single sheet, the record material is referred to as "self-contained" system and develops image color where the pressure is applied.

As a modification of pressure-sensitive marking system, Japanese Patent No. 511,757 (which corresponds to U.S. Pat. application Ser. No. 392,404, filed on August 27, 1964) discloses a recording sheet, in which minute capsules containing liquid solvent are coated on one surface of a sheet support and both of the chromogenic material and the acidic polymer are coated on or impregnated in same sheet or other sheet in solid condition.

There is thermo-responsive record sheet as a mark-forming system utilizing an electron donor-acceptor color-forming reaction. For example, Japanese Patent Application No. 14,039 of 1970 (which corresponds to U.S. Patent application Ser. No. 554,565 filed on June 1, 1966) discloses a temperature-responsive record material comprising a supporting sheet material having crystal violet lactone and a phenolic material solid at room temperature but capable of liquefying and/or vaporizing at normal thermographic temperatures, said lactone and phenolic material being further capable of producing a mark-forming reaction upon reactive contact.

The novel compounds of the invention are widely used for above-mentioned mark-forming systems as a colorless chromogenic compound, i.e. electron donor and gives many excellent advantages.

According to the present invention, the above-mentioned known techniques for the production of the recording sheet are utilized using the above-mentioned fluoran compounds as a coloring material alone or in admixture with various known coloring materials to obtain the recording sheet which can form red, bluish violet, blue, blue black or black color.

Also, it is effective for improving the color forming property and fastnesses to light and moisture of developed images to used a metal or metallic compound together with the electron-acceptor.

Thus, metals or metallic compounds such as manganese, nickel, cobalt, iron, zinc, copper, cadmium, mercury, silver, platinum, etc. are effective. Specific examples of the metallic compounds include salts and acid salts such as copper sulfate, ferrous sulfate, manganese sulfate, cobalt sulfate, zinc sulfate, nickel acetate, etc., basic salts such as cadmium hydroxide and oxides such as zinc oxide. They show particularly good results.

DETAILED DESCRIPTION OF THE PREFERRED EMBODIMENT

The following examples serve to illustrate the invention in more detail although the invention is not limited to the examples. Unless otherwise indicated, the amounts of the components are designated in parts by weight.

EXAMPLE 1

8.72g of 4-amino-8-diethylaminobenz[a]fluoran and 21.4g of benzyl bromide were dissolved in 50g of N,N-dimethylformamide. The solution was maintained at 70° – 80°C for 3 hours, and then further maintained for another 2 hours in the presence of sodium hydrogencarbonate.

After addition of 200 g of water, unreacted benzyl bromide was removed or decomposed by steam distillation in weakly alkaline solution. After cooling, the resultant solid was filtered and extracted with 600g of chloroform. The extract was condensed to obtain a white solid product, which was then recrystallized from benzene-ethanol solution.

Thus, 4-dibenzylamino-8-diethylaminobenz[a]fluoran was obtained in a yield of 92% which showed a melting point of 202°–203°C. This compound formed reddish violet color on silica gel. The product compound is represented by the following formula:

the mixture was adjusted to about 7.0.

The precipitate was filtered, washed with cold water, dissolved in 500g of chloroform, dehydrated with 50g sodium sulfate to which was added 5g of activated charcoal. The chloroform solution was filtered and concentrated under reduced pressure to obtain the crystals, then recrystallized from benzene. Thus, 27.9g of 4-diethylamino-8-diethylaminobenz[a]fluoran was obtained as white crystal which showed a melting point of 187° to 189°C. This compound produced reddish

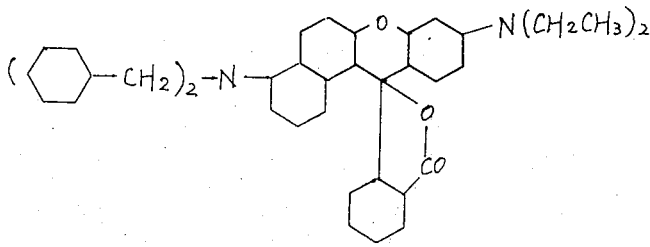

EXAMPLE 2

140 grams of conc. sulfuric acid was charged into a four-neck flask provided with a stirrer, a thermometer and a condenser. 123.0g of 5-diethylamino-2-naphthol and 31.3g of 2-(2-hydroxy-4-diethylaminobenzoyl)-benzoic acid were added to it with cooling. The mixture was heated to 70° to 80°C for 5 hours with stirring. After cooling the reaction mixture was poured into 700g of ice water. About 300g of 43% NaOH was added to the mixture to be hydrolyzed and the pH of violet color on silica gel. The product compound is presented by the formula:

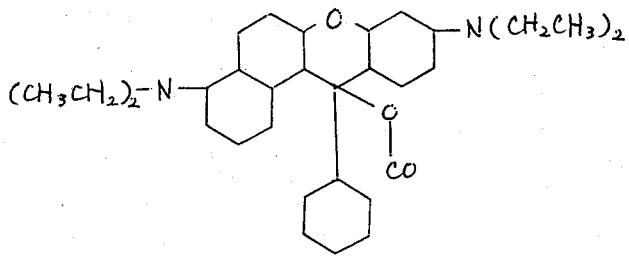

EXAMPLES 3 – 11

Table 1 illustrates various product compounds at the column C which were synthetized from different reactants respectively indicated at the columns A and B according to the similar process to that in Example 2. The shade of each of the product compounds is also indicated at the column D.

Table 1

| Example No. | A Reactant | B Reactant | C Product Compound | D Shade |
|---|---|---|---|---|
| 3 | (structure with NHCH₃ and OH) | (structure with OH, CO, COOH, (CH₃)₂N) | (structure with CH₃NH, O, N(CH₃)₂, CO) | blue |

Table 1—Continued

| Example No. | A Reactant | B Reactant | C Product Compound | D Shade |
|---|---|---|---|---|
| 4 | | | | ditto |
| 5 | | | | ditto |
| 6 | | | | bluish violet |
| 7 | | | | reddish violet |
| 8 | | | | dark red |
| 9 | | | | blue |
| 10 | | | | bluish violet |

Table 1 —Continued

| Example No. | A Reactant | B Reactant | C Product Compound | D Shade |
|---|---|---|---|---|
| 11 | (structure with N(CH₃)₂ and HO groups on decalin) | (structure with C₂H₅, CH₃, N, CO, COOH) | (fluoran product structure with (CH₃)₂N, C₂H₅, CH₃ substituents) | reddish violet |

EXAMPLES 12 to 22

Table 2 illustrates further various product compounds at the column C which were synthetized by the reaction between the compounds indicated at the column A and the fluorans indicated at the column B, respectively, according to the similar process to that in Example 1 except that the compounds indicated at the column A are used instead of benzyl bromide. The shade of each of the product compounds is also indicated at the column D.

| Example No. | A Alkylating agent | B Fluoran | C Product Compound | D Shade |
|---|---|---|---|---|
| 12 | $CH_2=CH-CH_2Br$ | (fluoran with $H_2N$ and $N(CH_3)_2$) | (fluoran with $(CH_2=CHCH_2)_2N$ and $N(CH_3)_2$) | reddish violet |
| 13 | $CH_3CH=CH-CH_2Br$ | (fluoran with $H_2N$ and $N(C_3H_7)_2$) | (fluoran with $(CH=CHCH_2)_2N$—$CH_3$ and $N(C_3H_7)_2$) | ditto |
| 14 | (cyclohexyl)-CH=CH-CH₂Cl | (fluoran with $NH_2$ and $N(C_3H_7)_2$) | (fluoran with $(CH=CHCH_2)_2N$—cyclohexyl and $N(C_3H_7)_2$) | ditto |
| 15 | $CH\equiv C-CH_2Br$ | (fluoran with $H_2N$ and $N(CH_3)_2$) | (fluoran with $(CH\equiv C-CH_2)_2N$ and $N(CH_3)_2$) | reddish violet |
| 16 | $CH_2=C(CH_3)-CH_2Cl$ | (fluoran with $H_2N$ and $N(C_2H_5)_2$) | (fluoran with $(CH_2=C(CH_3)-CH_2)_2N$ and $N(C_2H_5)_2$) | ditto |

| Example No. | A Alkylating agent | B Fluoran | C Product Compound | D Shade |
|---|---|---|---|---|
| 17 | $CH_3-C\equiv C-CH_2Br$ | | | ditto |
| 18 | $CH_2=CHCH_2Br$ | | | reddish violet |
| 19 | $CH_3\text{-}\diagup\text{-}SO_2OCH_3$ or $(CH_3O)_2SO_2$ or $(CH_3O)_3PO$ | | | ditto |
| 20 | $CH_3\text{-}\diagup\text{-}SO_2OC_2H_5$ or $(CH_3CH_2O)_2SO_2$ | | | ditto |
| 21 | $CH_3\text{-}\diagup\text{-}SO_2OCH_2CH_2OCH_3$ | | | reddish violet |
| 22 | $CH_2=CHCN$ | | | ditto |

Various chromogenic compounds of the invention were tested for fastness of color formed on several recording paper, the results of which are reported in Table 3. Column A indicates the specific chromogenic compound used, column B identifies the electron-acceptor and column C indicates the shade observed. The following procedure was used.

EXAMPLES 23 to 30

3 parts by weight of the specific benz[a]fluoran was dissolved in 100 parts by weight of iso-propylated diphenyl at about 100°C. Meanwhile, 25 parts by weight of pigskin gelatin having an iso-electric point of pH 8 and 25 parts by weight of gum arabic were dissolved in 300 parts by weight of water at 50°C. The above solution of the fluoran compound was added to the gelatin-gum arabic solution with continuous stirring to make an emulsion. After the addition of 100 parts by weight of warm water, acetic acid was added to the emulsion to adjust the pH to 4 – 4.5. At this stage, the gelatin and gum arabic were deposited around the oil droplets to make a capsule.

After gelation of the wall of the capsule by cooling at about 10°C, 10 parts by weight of 25% aqueous solution of glutaraldehyde was added to harden the wall. The coating composition containing the thus prepared microcapsules was applied onto the one side of a paper of 45g/m² by weight of 5g/m² on dry basis. The other side of the paper was coated with a coating composition containing 100 parts by weight of acidic clay, which was dispersed in 200 parts by weight of water, and 30 parts by weight of styrene-butadiene latex having a solid content of 50% by weight of 5g/m².

The thus obtained recording papers were superimposed in such a way that the layer containing the microcapsules was faced to the layer of the other paper containing acidic clay. The obtained color image did not change in color by the effect of water, alcohol or direct sunlight.

parts by weight of solvent represented by the formula,

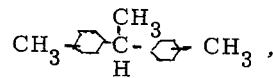

at 100°C. The resultant solution was dispersed into 500 parts by weight of 7% gelatin solution to make an emulsion at 60°C. 350 parts by weight of 10% solution of gum arabic and 550 parts by weight of hot water were added to the emulsion. Then, 10% solution of acetic acid was slowly added to emulsion with continuous stirring at 50°C to adjust the pH to 4.0 – 4.3. After cooling the emulsion to the temperature below 10°C, 200 parts by weight of 50% dispersion of titanium dioxide having a particle size of 0.2 – 0.5μ was added to the above emulsion mixture with continuous stirring. Then, 38 parts by weight 37% formalin solution was added to the mixture, and the pH of the mixture was adjusted to 10.0 – 10.5 by addition of 10% solution of sodium hydroxide. The resultant mixture is referred to as "A liquid".

On the other hand, 20 parts by weight of zinc oxide and 40 parts by weight of 28% ammonia water were added into 400 parts by weight of water. 200 parts by weight of acidic clay was dispersed in the mixture and 1 part of sodium alginate was dissolved in the mixture. Then, 100 parts by weight of 10% polyvinylalcohol solution was added to the dispersion mixture. After the dispersion was mixed with the above "A liquid", 25 parts by weight of 10% polyvinylalcohol and 100 parts by weight of pulp powder were added to the mixture to make a coating composition. The obtained coating composition was applied onto one side of a paper of 40g/m² by weight of 10g/m² on dry basis. The resulting Table 3

| Example Number | A<br>Chromogenic Compound | B<br>Electron-acceptor | C<br>Shade |
|---|---|---|---|
| 23 | 4-dibenzylamino-8-diethyl-aminobenz[a]fluoran | acidic clay | reddish violet |
| 24 | 4-benzylamino-8-diethylamino-benz[a]fluoran | " | blue |
| 25 | 4-propargylamino-8-diethylaminobenz[a]fluoran | " | " |
| 26 | 4-N-acetylamino-8-dimethyl-aminobenz[a]fluoran | " | red |
| 27 | 4-diallylamino-8-diethyl-aminobenz[a]fluoran | " | reddish violet |
| 28 | 4-dimethylamino-8-dimethyl-aminobenz[a]fluoran | " | " |
| 29 | 4-amino-8-{N-ethyl-n-(p-methyl-phenyl)}aminobenz[a]fluoran | acidic clay | blue black |
| 30 | 4-dimethylamino-8-{N-ethyl-N-(p-methylphenyl)}aminobenz-[a]fluoran | activated clay | reddish violet |

EXAMPLE 31

4 parts by weight of 4-(p-chlorobenzyl)amino-8-dimethylaminobenz[a]fluoran was dissolved in 100 pressure-sensitive recording paper is a so-called "Self-contained" type recording paper. When pressure was applied onto the surface, blue color was instantly formed which did neither change nor disappear by the effect of sunlight and/or moisture.

EXAMPLE 32

In the same manner as in Examples 23 – 30, pressure-sensitive recording paper was obtained using 2 parts by weight of 2-dibenzylamino-8-diethylaminobenz[a]fluoran, 1 part by weight of 4-acetylamino-8-diethylaminobenz[a]fluoran which forms red color and 1.5 parts by weight of 3,6-dimethoxyfluoran which forms yellow color as electron donating chromogenic compounds. Black color image was obtained by the application of pressure which maintained the original color during storage for a long period of time.

EXAMPLE 33

A thermo-responsive (or heat sensitive) recording material is manufactured by following manner. 20 parts by weight of 4-benzylamino-8-diethylamino-benz[a]-fluoran, 15 parts by weight of 3-diethylamino-6-methylfluoran, 150 parts by weight of a 10% aqueous solution of polyvinyl alcohol and 65 parts by weight of water were dispersed in a high shear mixer (Component A). 35 parts by weight of Bisphenol A, 150 parts by weight of water were dispersed in a high shear mixer (Component B). 3 parts by weight of Component A and 67 parts by weight of Component B were combined and coated on the paper sheet by weight of 5g/m² on dry basis. The resulting may be used alone as a copy-receiving sheet by being served with a pattern of heat from front or back, as by a thermographically-heated original document, by trace of a hot stylus, by hot type, or by any other means giving a heat pattern by conduction. The obtained image of this sheet is black.

COMPARATIVE EXAMPLES

The following examples are comparison of certain tetrachlorinated chromogenic compounds and one unchlorinated fluoran described in U.S. Pat. No. 3,654,314 with the compounds of the present invention. In all instances the comparison or known compounds are represented by a letter, such as B, whereas the compounds of the present invention are represented by a numerical. The following comparisons were made:
1. Solubility in an Oil
   The compounds were dissolved in the oil represented by the formula,

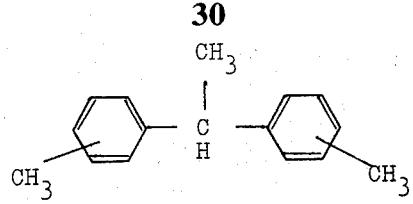

(SAS-296, product of Nippon Petrochemicals Co., Ltd.), and oil commonly used for a pressure-sensitive recording sheet, to produce 3% and 5% solution. The solutions were allowed to stand, and observed after 1 hour, 3 days and 7 days, respectively.

2. Adsorption Spectrum
   Adsorption spectrum was determined in the mixture solution of acetic acid with ethanol (1:4). In the case of the compound represented by the formula,

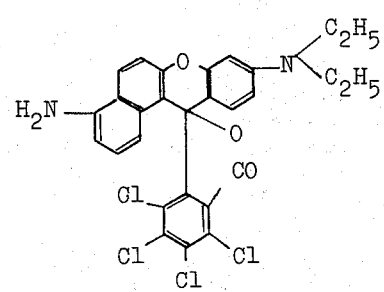

adsorption spectrum was determined in the mixture of acetic acid with water (1:4) because this compound showed only yellow color ($\lambda$ max = 420m$\mu$, $\epsilon$ = 1.3×10⁴) in the mixture solution of acetic acid with ethanol.

3. Light Resistance
   The solution (3%) used in the solubility test was applied onto the acid clay-coated surface of the paper which was obtained in Example 23 to produce color. The thus-obtained color was exposed to direct sunlight to evaluate its light resistance.

The results of these comparisons are reported in the following Table, the values reported being color of the compound as developed on acid clay-coated paper, the adsorption spectrum, both as to adsorption maximum and molecular extinction coefficient, and solubility in oil at 3% and 5% measured after 1 hour, 3 days and 7 days. Sunlight resistance was also reported. The results demonstrate that the compounds of the present invention are relatively soluble in a solvent; this facilitates preparation of the recording paper and provides for a deep image on the paper. As indicated by the molecular extinction coefficient the compounds of the invention produce a deep, dark color, which is desirable, and different shades of color may be produced, i.e., blue-black, greenish-black or reddish-brown, depending upon the nature and position of the amino substituent group. Also these compounds exhibit excellent resistance to light. On the contrary, the tetrachlorinated compound A is very poor in image density, that is the extinction coefficient is considerably small. In the unchlorinated compound B, relatively poor oil solubility is shown as well as poor light resistance.

TABLE

| Chemical Structure of Compound | Color Developed on Acid Clay Coated Paper | Adsorption Adsorption Maximum ($\lambda_{max}$) (mμ) | Spectrum Mol. Extinction Coefficient (ε) | Solubility in Oil | | | | | | Sun-Light Resistance |
|---|---|---|---|---|---|---|---|---|---|---|
| | | | | After 1 Hour | 3% After 3 Days | After 7 Days | After 1 Hour | 5% After 3 Days | After 7 Days | |
| A (structure with NH₂, Cl₄, N(C₂H₅)₂) | bluish violet (a little) light | 543 | 0.5×10⁴ | no crystals deposited | " | " | " | a few crystals deposited | " | color changed or faded after 2 hours |
| B (structure with NH₂, N(C₂H₅)₂) | violet | 605 | 2.2×10⁴ | *many crystals deposited | " | " | " | scarcely dissolved | — | after 1 hour |
| (structure with PhNHCH₂, N(C₂H₅)₂) | blue | 630 | 2.9×10⁴ | no crystals deposited | " | " | " | a few crystals deposited | " | after 2 to 3 hours |
| (structure with N(CH₂Ph)₂, N(C₂H₅)₂) | reddish violet | 570 | 2.6×10⁴ | no crystals deposited | " | " | " | a few crystals deposited | " | after 5 to 6 hours |
| (structure with N(C₂H₅)H, N(C₂H₅)₂) | bluish black | 635 | 1.9×10⁴ | no crystals deposited | " | " | " | a few crystals deposited | many crystals deposited | after 2 hours |
| (structure with N(C₂H₅)₂, N(C₂H₅)₂) | reddish violet | 565 | 1.6×10⁴ | no crystals deposited | " | " | " | a few crystals deposited | | after 3 to 4 hours |
| (structure with NHCH₃, N(C₂H₅)₂) | blue-black | 635 | 1.4×10⁴ | no crystals deposited | " | " | " | a few crystals deposited | many crystals deposited | after 2 hours |
| (structure with N(CH₃)₂, N(C₂H₅)₂) | reddish violet | 570 | 2.2×10⁴ | no crystals deposited | " | " | " | a few crystals deposited | | after 3 to 4 hours |

What is claimed is:
1. The compound of the formula,
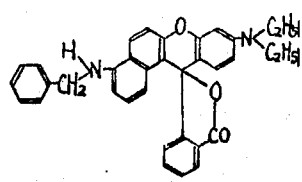
2. The compound of the formula,
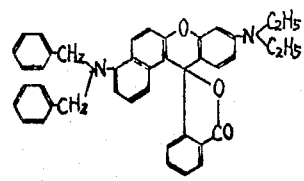
* * * * *